United States Patent [19]
Taboada et al.

[11] Patent Number: 5,112,328
[45] Date of Patent: May 12, 1992

[54] METHOD AND APPARATUS FOR LASER SURGERY

[75] Inventors: John Taboada; Robert H. Poirier, both of San Antonio, Tex.

[73] Assignee: Refractive Laser Research & Development Program, Ltd., San Antonio, Tex.

[21] Appl. No.: 563,849

[22] Filed: Aug. 7, 1990

Related U.S. Application Data

[63] Continuation of Ser. No. 148,425, Jan. 25, 1988, abandoned.

[51] Int. Cl.⁵ .............................................. A61N 5/02
[52] U.S. Cl. ......................................... 606/4; 606/5; 606/13; 606/15; 606/17; 606/19; 128/395; 128/898
[58] Field of Search ............... 128/395, 397, 398, 898; 606/10—19, 5, 4; 604/27, 30; 219/121.6, 121.67, 121.68, 121.69, 121.73, 121.75, 121.78-121.8, 212.83, 121.85

[56] References Cited

U.S. PATENT DOCUMENTS

| | | | |
|---|---|---|---|
| 2,843,112 | 7/1958 | Miller | 128/6 |
| 4,126,136 | 11/1978 | Auth et al. | 128/303.1 |
| 4,273,109 | 6/1981 | Enderby | 128/303.1 |
| 4,391,275 | 7/1983 | Frankhauser | 128/303.1 |
| 4,470,407 | 9/1984 | Hussein | 128/398 |
| 4,538,608 | 9/1985 | L'Esperance, Jr. | 128/303.1 |
| 4,583,539 | 4/1986 | Karlin et al. | 128/303.1 |
| 4,592,353 | 6/1986 | Daikuzono | 128/303.1 |
| 4,681,104 | 7/1987 | Edelman | 128/303.1 |
| 4,718,418 | 11/1988 | L'Esperance, Jr. | 128/303.1 |
| 4,729,372 | 3/1988 | L'Esperance, Jr. | 128/303.1 |
| 4,729,373 | 3/1988 | Peyman | 128/303.1 |
| 4,732,448 | 3/1988 | Goldenberg | 128/6 |
| 4,744,360 | 5/1988 | Bath | 128/397 |
| 4,748,631 | 5/1988 | Bjorklund | 372/21 |
| 4,761,786 | 8/1988 | Baer | 372/13 |

FOREIGN PATENT DOCUMENTS

| | | | |
|---|---|---|---|
| 144764 | 6/1985 | European Pat. Off. | 128/303.1 |
| 172490 | 2/1986 | European Pat. Off. | 128/303.1 |
| 207648 | 1/1987 | European Pat. Off. | 128/303.1 |
| 253734 | 1/1988 | European Pat. Off. | 128/303.1 |
| 8700748 | 2/1987 | World Int. Prop. O. | 128/303.1 |
| 8707156 | 12/1987 | World Int. Prop. O. | 128/303.1 |
| 8707449 | 12/1987 | World Int. Prop. O. | 372/3 |

Primary Examiner—David Shay
Attorney, Agent, or Firm—Mason, Fenwick & Lawrence

[57] ABSTRACT

Apparatus and method for laser surgery in which laser energy, pulsed or continuous, is focussed to a focus spot of ten to thirty microns which is located within tissue, or the like to cause highly localized heating. The pulsed radiation is in the TEM(oo) mode, has a wavelength of approximately 1064 nanometer, the pulses being not in excess of 100 nanoseconds and the pulse rate being approximately 2000 per second. Where the laser beam is continuous or pulsed, it has a wavelength of approximately 1400 to 1800 nanometer, or in photoablative modes, having a wavelength of 190 to about 300 nanometers. The focus spot may be caused to move relative to the axis of a handpiece; and to liquid may flow across the exposure site to remove debris. A handpiece may have an endoscope including a glass contact tip at its distal end to receive light and to acquire an image of the exposure site probes for eye surgery include a quartz rod in a sheath, the quartz rod having a beveled distal end surface through which the laser radiation is emitted and may have infusion and aspiration passages with ends coplanar with the beveled end surface of the quartz rod.

62 Claims, 7 Drawing Sheets

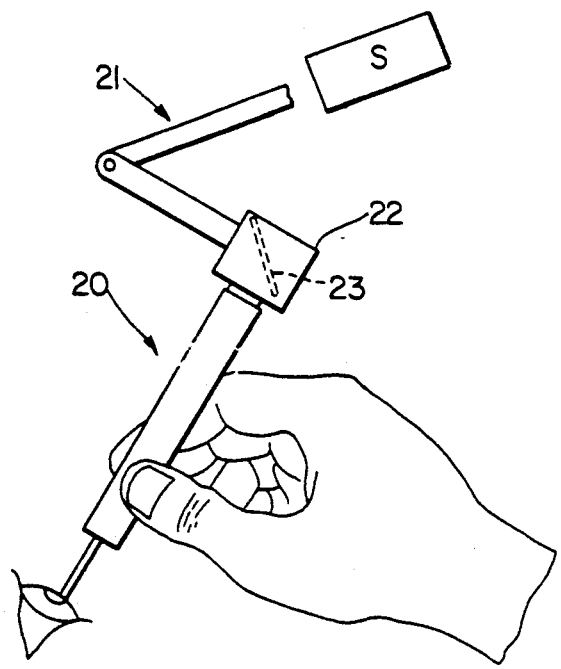
FIG. 1
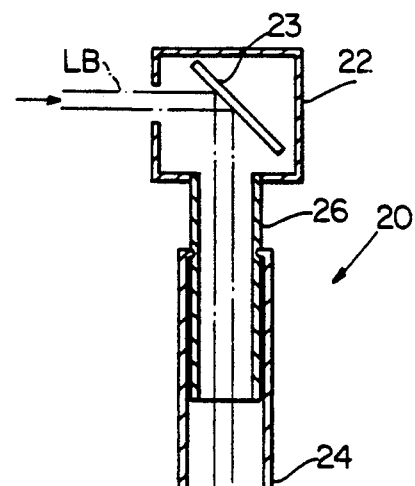
FIG. 2
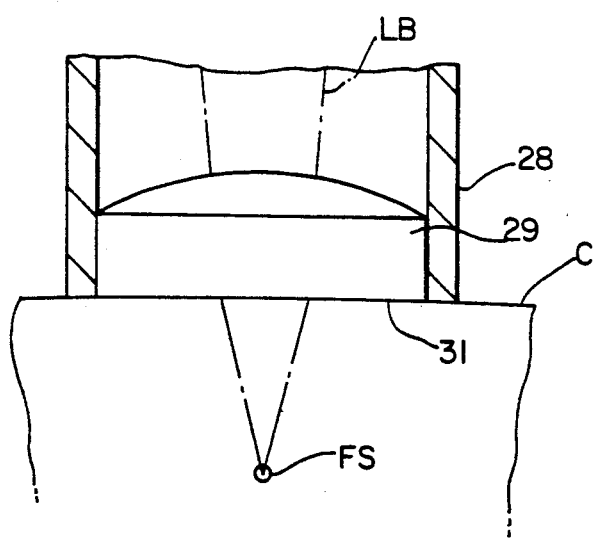
FIG. 3
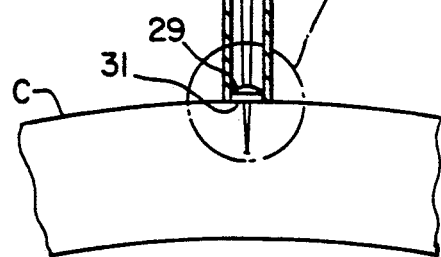

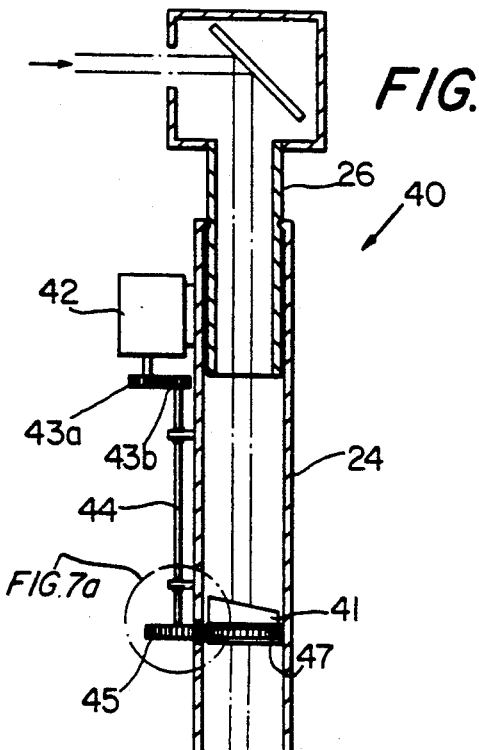
FIG. 7
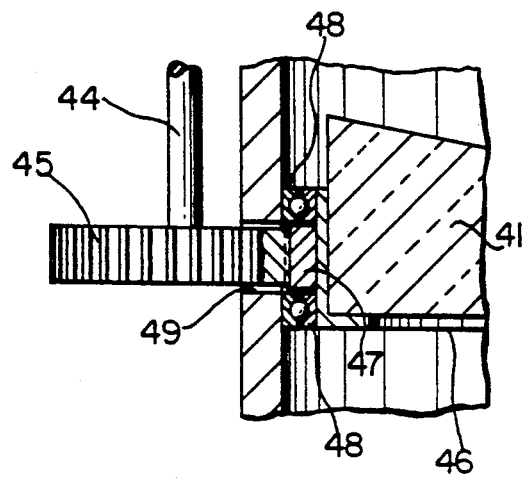
FIG. 7a
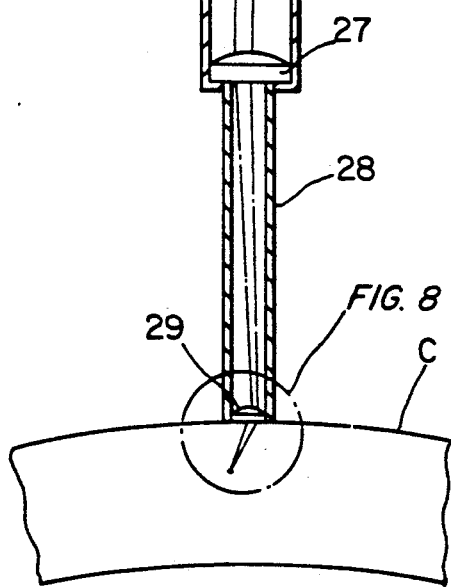
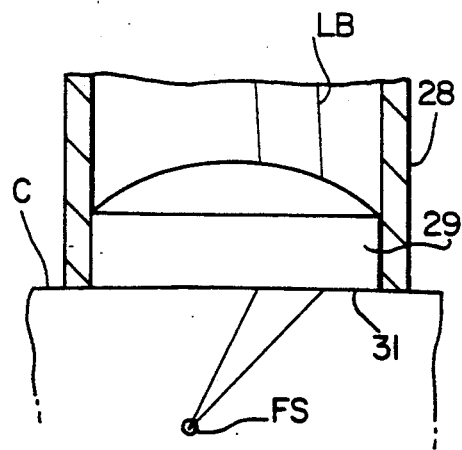
FIG. 8

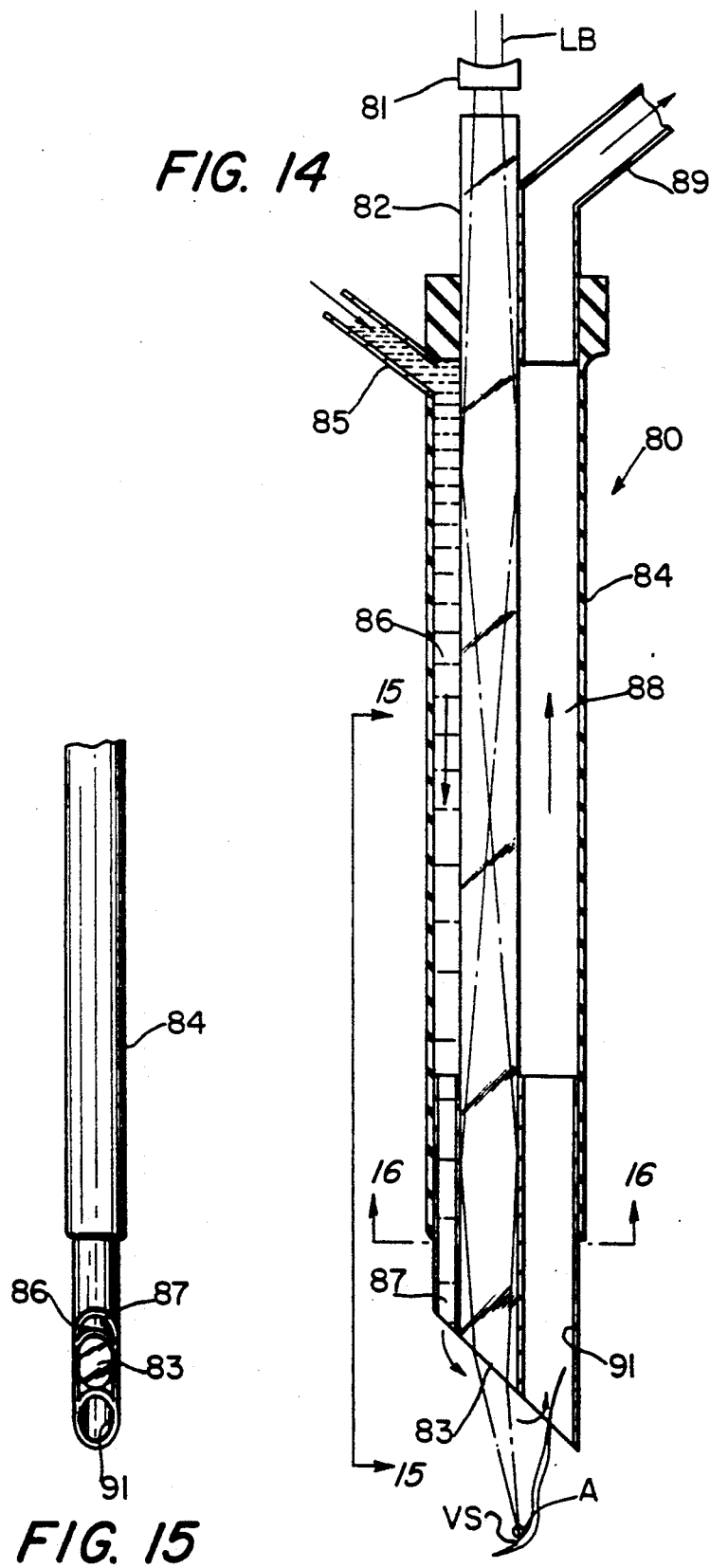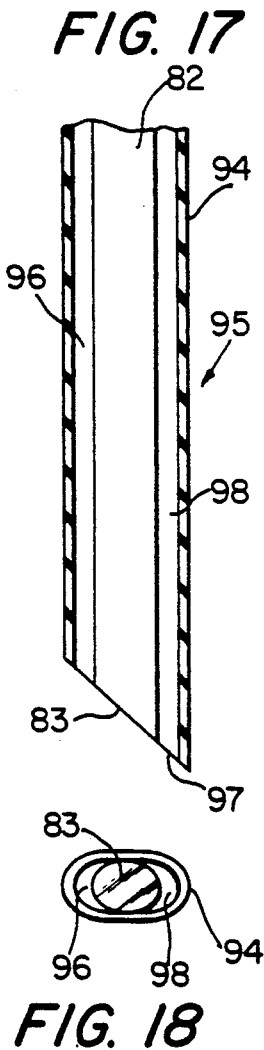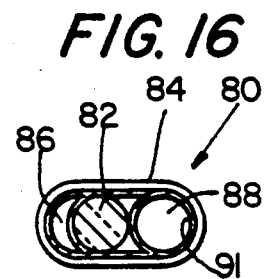

METHOD AND APPARATUS FOR LASER SURGERY

This application is a continuation of application Ser. No. 07/148,425 filed Jan. 25, 1988 now abandoned.

BACKGROUND OF THE INVENTION

This invention relates to method and apparatus for effecting surgery through the application of a laser beam.

The present method and apparatus are particularly applicable to the delivery of laser energy for performing various surgical procedures. These include eye surgery, and more particularly cornea, cataract or vitreal surgery, and various dental procedures.

It is recognized that lasers have experienced widespread use in the medical field, for such purposes as cutting, cauterizing, melting and ablating tissue. In order to affect the tissue to the greatest degree, it has been found that one or more of three conditions must be met:

(a) The laser must be delivered in high powered pulses or with high continuous power;

(b) The laser must be tuned to the extreme violet end of the spectrum where the photon absorption is high in organic substance; or (c) The laser must be tuned to the extreme infrared end of the spectrum where water, a major constituent of living tissue, is a strong absorber.

Condition (a) functions through non-linear optical processes such as dielectric breakdown. See for example "Laser Induced Electric Breakdown in Solids" by N. Bloembergen, IEEE. J. of Quantum Electronics, Volume QE10 Number 3, March 1974, pages 375 to 386. The non-linear process creates a finely localized absorption site since the resulting plasma is usually opaque to the laser beam.

The noted conditions are extreme conditions which have resulted in the inability of optical components to handle the laser energy delivered.

A particular application of the present invention is in keratoplasty. There are various known keratoplasty techniques which depend on a deposition of heat energy, i.e., heat induced keratoplasty. The principle behind heat induced keratoplasty is that of producing shrinkage in the principal protein of the clear corneal medium, collagen. When type I collagen is heated above 62° C., there is a break in the collagen cross links, and contraction of the collagen occurs. Collagen contraction, in turn, modifies the corneal curvature. Original approaches to heat delivery were dependent on direct contact of the corneal surface with a heater. The clear disadvantage of this technique is that unnecessary collateral heat damage of anterior layers of the cornea takes place. Another approach is by radio frequency radiation heating of the mid-stromal layer by means of an antenna-like probe, as described by J.D. Doss, et al. U.S. Pat. No. 4,326,529. The method of Doss et al involves heating the central stroma with a radio frequency electrode probe, at the same time cooling the surface of the cornea with a saline solution. A clear disadvantage of this approach is that the heat deposition is not easily localized in the three-dimensional space of the cornea, because of the use of the radio frequency wavelengths required by this method. The application of radio frequency radiation resulted in an insufficiently localized distribution of the heat energy.

Another application of the present invention is in cataract surgery. In one technique, the lens is removed by suction, after having been emulsified by an ultrasonic probe, known as a phacoemulsifier. The ultrasonic energy causes fragmentation of the human lens nucleus, so that it could then be aspirated through fine tubing and thereby removed from the eye. There are, however, certain limitations of this method of cataract surgery, which is at present the prominent method used in the United States. These limitations include the possibility that the high ultrasonic frequency fragmentation may result in the fragmentation of the nucleus of the lens in large multiple pieces, thereby complicating the actual handling and separation of the cortex. Other undesirable effects include potential burns to the cornea and possible battering effects of the nucleus against the corneal endothelium, resulting in corneal endothelial decomposition requiring penetrating keratoplasty. The cause of this limitation is primarily a result of the difficulty of controlling the energy delivery.

Another advance in opthamolic surgery is in the field of vitreoretinal surgery. There has been devised a procedure in which a vitreous infusion suction cutter was provided for the purpose of removal of vitreous from the human eye through the pars plana. The vitreous infusion suction cutter is basically comprised of various scissor-like cutting devices which are combined with a suction element for the removal of fragments in the vitreous. Limitations of this apparatus are significant and are associated with the difficulty of actually moving the vitreous bands and tissue into the cutting ports safely without jeopardizing the adjacent retina. Also, there is the potential for mechanically separating the retina, producing holes by means of this mechanical cutting device. The cutting of fine membrane attached to the surface of the retina with, such a large instrument, typically 3 mm in diameter, makes the problem of vitreoretinal membrane stripping, epiretinal membrane mobilization and repair of difficult traction, retinal detachments a long process involving many attendant undesirable complications associated with such instrumentation.

The prior art of surgery in the human body abounds with demands for precise cutting, cauterizing and removal of tissue of very small dimensions. Such surgical procedures in general require handheld surgical instruments used under an operating microscope. Critical fields are neurological and renal surgery where precise control of the cutting instrument is required in order to avoid collateral damage which could prove extremely harmful. The traditional surgical blade has the limitation of limiting visibility of the surgical site from lateral view, and with it there is limited control of the depth of cut.

Among the laser apparatus used for surgery as disclosed in prior art patents is Smith 4,122,853 which discloses a carbon dioxide infrared laser for use in photocoagulation or localized surgical procedures. A probe is provided having a lens system which includes first and second lenses remote from the distal end of the probe, and which serve to receive a relatively large diameter beam of collimated light and to reduce it to a smaller diameter beam of collimated light: a lens at the distal end or tip of the probe has either two planar surfaces, or an external planar surface and an internal curved surface which focus the beam on the window outer surface. The probes disclosed are equipped to provide for an endoscope, to view the site, and fluid passage for fluid flow through the probe.

Choi 4,207,874 discloses an apparatus using a laser beam, conducted through a fiberoptic bundle to a thrombus to burn a tunnel through the thrombus.

Muncheryan 3,382,343 and Muncheryan 3,383,491 teach laser beam apparatus with optical systems for focussing the laser beam on a workpiece: the lens position in this apparatus is fixed so that the plane of the laser beam coincides with the surface of the workpiece in contact with the instrument tip. In Muncheryan 3,381,510, a laser beam instrument is provided in which there is a movable lens element, to permit displacement of the focal plane to any desired distance remote from the tip of the probe, so as to provide a cutting operation on body tissue, for example, with the tip of the probe remote from the body to avoid contamination.

Goldenberg 4,641,912 discloses a system for delivering an excimer laser beam for angioplasty, including an optical fiber with the distal end formed as a lens to increase the density of the energy after it has emerged from the fiber by reducing its cross-section: in use, the end of the fiber is positioned at a distance from the obstructing lesion, so that the focal plane is at the surface thereof. Hett 4,072,147 is another example of a laser beam focussed on an object for therapeutic purposes.

In the field of dentistry, for decades the removal of tooth material has been by use of rotary cutting instruments, evolving from a motor driving the tool through a belt or cord, to more recent developments in which the tool is driven at higher speeds by an air turbine. Although these instruments have been effective in the removal of tooth material, they have experienced certain disadvantages, such as the following:

(1) The instrument obscures the view of the site being treated.
(2) The dimensions of the cutting components, such as burrs, bits, etc. often are too large for the desired precision of the procedure.
(3) The instruments are heavy and bulky.
(4) The instruments require excessive amounts of energy to operate them, a portion of which is often delivered to the patient, making the patient very uncomfortable as the excess energy is transmitted to non-local nerve endings.

SUMMARY OF THE INVENTION

There is provided a method and apparatus for microsurgical and intra-oral dental purposes which are particularly applicable to intrastromal keratomeleusis, intrastromal keratotomy, and excimer radial keratotomy for the correction of myopia, astigmatism, hyperopia, or combinations of refractive errors. Laser energy of predetermined characteristics is focussed to a focus spot having a diameter of a few microns which is located a predetermined distance, such as one millimeter, beyond a lens at the distal end of a handpiece, the focus spot being located, for example, in the intrastromal layer. The lens at the distal end of the handpiece, of sapphire, is placed against the cornea, and localized heating in the intrastromal layer modifies the corneal curvature to effect keratoplasty or keratotomy. Laser energy is delivered in the TEM(oo) mode, the laser beam having a wavelength of approximately 1.0 to 2.0 microns, and in one embodiment a repetitively Q-switched YAG laser emits at 1064 nanometer wavelength. The pulses have a duration of about 70 nanoseconds, and pulsing is at the rate of approximately 2000 per second. Alternatively, continuous radiation having a wavelength in the range of 1400-1800 nanometers is generated by using a Neodymium YAG laser to pump f-centers in sodium chloride crystals, or a YAG laser is used to stimulate Raman scattering in a hydrogen gas cell which emits at 1900 nanometers.

In a preferred embodiment, the handpiece contains an optical wedge which is oscillated or rotated in order to oscillate or rotate the focus spot while the handpiece is stationary.

In another embodiment, a focussing lens of a handpiece is spaced from the distal end, the end portion of the handpiece narrowing or tapering towards the distal end, there being a fluid inlet into the terminal portion of the handpiece, with fluid flowing in the tapering terminal portion and exiting through escape channels at the distal end, the laser beam travelling through fluid flowing through the handpiece terminal portion.

In a related embodiment, the terminal portion of a handpiece is provided with a contact tip of glass, light being delivered to the penetration point through a single mode optical fiber and the contact tip, and an optical fiber bundle receiving an image of the penetration point from a reflective surface of the contact tip for passage of it to a display. The contact tip is provided with escape channels at its distal end for the escape of saline solution passed through the terminal portion of the handpiece.

In embodiments used for conducting cataract or vitreal surgery in which photoablative laser radiation is used, a probe has a quartz rod to which the radiation is coupled, the probe containing an infusion passage and an aspirating passage on either side of the beveled distal end surface of the quartz rod, water flowing across the beveled distal end surface of the quartz rod from the infusion passage to the aspirating passage.

Among the objects of the present invention are the provision of a method and apparatus for the performance of surgical procedures by the delivery of high powered laser radiation in the fundamental transverse mode to highly localized focus sites within tissue, such as in the midcorneal stroma, by application of a focus spot of a few micron diameter.

Another object is to provide such a method and apparatus in which portions of the tissue adjacent to the focus spot are relatively undisturbed.

Yet another object is to provide a method and apparatus for the localized delivery of short pulse photo-ablative laser energy to a diffraction limited spot size on dental sites.

Another object is the provision of a handpiece for the delivery of laser energy, together with means for obtaining an image of the site.

Another object of the invention is to provide a method and apparatus for delivering laser energy in localized sites using either pulsed or continuous radiation having a near infrared wavelength of 1.0-2.0 microns, or an ultraviolet wavelength of about 190-300 nanometers.

Still another object of the invention is to provide a laser apparatus and method characterized by the delivery of high power laser radiation to a highly localized site within tissue, and with movement of the focus spot without movement of the handpiece.

Still another object is to provide an apparatus for delivering laser energy which includes the provision of fluid flow to remove debris caused by the application of the laser energy.

Yet another object of the invention is to provide apparatus useful in cataract or vitreal surgery in which laser energy is delivered through a probe containing a quartz rod, with provision for infusion and aspiration of fluent material.

Other objects and many of the attendant advantages of the method and apparatus of the present invention will be readily understood from consideration of the following specification, drawings and claims.

BRIEF DESCRIPTION OF THE DRAWINGS

FIG. 1 is a perspective view showing a handpiece in accordance with the present invention.

FIG. 2 is a longitudinal cross-sectional view of the handpiece of FIG. 1 engaging a cornea.

FIG. 3 is an enlarged view of the portions of FIG. 2 within circle 3 of FIG. 2

FIG. 7 is a view similar to FIG. 1 of a modification of the handpiece of FIG. 2.

FIG. 7a is an enlarged view of the structure within circle 7a of FIG. 7.

FIG. 8 is a diagrammatic view illustrating the operation of the handpiece of FIG. 7.

FIG. 14 is a longitudinal cross-sectional view of a photoablative terminal probe for cataract surgery.

FIG. 15 is a view taken on line 15—15 of FIG. 14.

FIG. 16 is a cross-sectional view taken on line 16—16 of FIG. 14.

FIG. 17 is a longitudinal cross-sectional view of an alternate embodiment of a photoablative probe for vitreal surgery.

FIG. 18 is an end view of the probe of FIG. 17.

DESCRIPTION OF THE PREFERRED EMBODIMENTS

Figure 4:
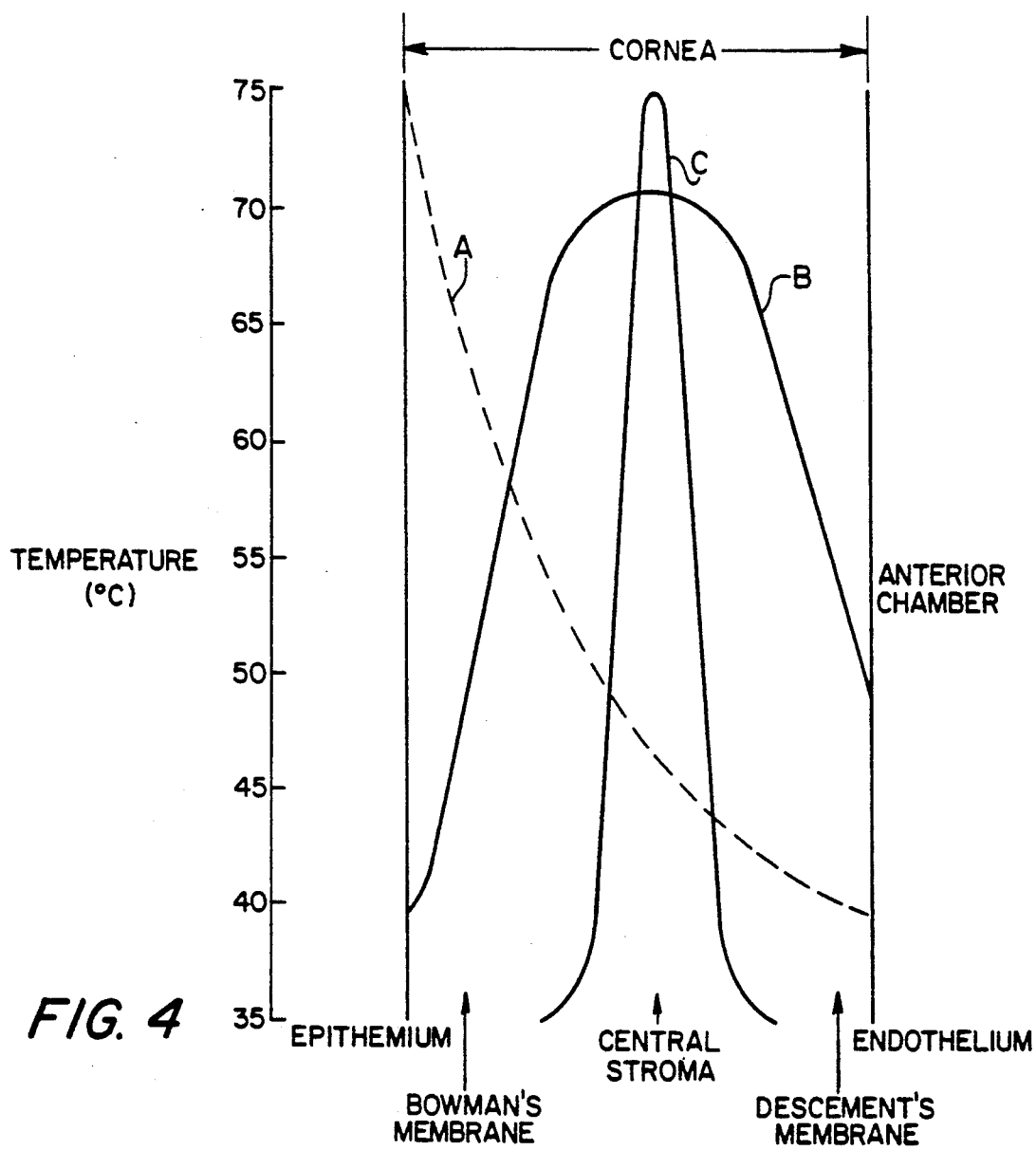
FIG. 4 is a chart showing results achievable with the method and apparatus of the present invention.

Referring now to the drawings, wherein like or corresponding reference numerals are used for like or corresponding parts throughout the several views, there is shown in FIG. 1 a handpiece 20 of generally cylindrical form, and supported by an articulated arm system 21 which contains prisms and hollow arms for transmitting and refracting laser energy from a laser source S. The handpiece 20 is shown being applied to the eye E of a patient. Handpiece 20 depends from a support block 22 having a prism 23 therein for refracting light originating from laser source S.

Referring to FIG. 2, the handpiece 20 includes an outer tube 24 rotatably mounted on an inner tube 26 which is connected to the support block 22. At the lower end of tube 24 of handpiece 20, there is a planoconvex focussing lens 27. Beyond lens 27, there is a terminal portion 28 of smaller diameter, within which is a second lens 29, lens 29 also being a plano-convex lens. In a preferred embodiment, the lens 27 is 6.3 mm diameter with a 30.7 mm focal length, and is positioned 23 to 26 mm from the lens 29. Lens 29 is a sapphire lens 1.5 mm in diameter and having a 1.0 mm focal length. In use, laser beam LB is reflected by prism 23 along the axis of the handpiece 20, and is focussed by the objective lenses 27 and 29, passing through air along its path until it exits from the lens 29. Lens 29 is held with the plano surface 31 thereof against the cornea C of the patient.

As shown in FIG. 3, with the plano surface 31 of lens 29 against the surface of cornea C, the residual fluid of the corneal surface optically couples lens 29 to cornea C. The laser beam radiation is in TEM(oo) mode and is diffraction limited: it is focussed as a focus spot FS, shown rotated 90° from its normal position for purposes of clarity, the focus spot FS being of minimum size, of a few, i.e., 3-5 microns diameter. The focus spot FS lies beyond or outwardly of handpiece 20, at a predetermined distance into the cornea from the outer surface thereof. The distance is determined by the focal lengths of lenses 27 and 29, which, in a preferred embodiment provided, is one millimeter. Thus, the focus spot FS is within the cornea C about 0.4-0.5 millimeter from the surface thereof.

Because of the extremely fine focus of the laser radiation, which is on the order of a few microns, the high field strength of the laser beam causes dielectric breakdown and plasma formation. In a preferred embodiment, the laser source S is a repetitively Q-switched CW lamp pumped Neodymium YAG laser, such as the Quantronics Model 117. The pulses are at a high pulse rate of about 2000 per second, and have a duration of about 70 nanoseconds or less. This source emits a laser beam having a wavelength of 1064 nanometer. The induced plasma shields the posterior layers of the cornea C, and deposits highly localized energy to the stromal fibers. This results in a cutting process. However, the outer and inner layers of the cornea C, the epithelium and the endothelium, are left intact due to the localized or restricted region into which the high energy focus spot FS is delivered. This permits rapid healing of the treated site. Thus, the handpiece 20 may be used for intrastromal keratomeleusis for the purpose of effecting and correcting myopia or myopic astigmatism. The handpiece 20 can be freely passed along and over the surface of the cornea C, so as to achieve a desired pattern of treatment loci.

FIG. 4 is a schematic diagram showing the temperature at various depths in the cornea due to different methods of application of energy. Line A shows the temperature distribution when a heated element is applied to the surface of the cornea, there being a temperature of approximately 75° C. at the surface of the cornea, the temperature dropping to approximately 40° C. at the endothelium layer. With the radiofrequency application method as described in Doss et al. 4,326,529, the temperature distribution is shown by line B; there is significant heating of Bowman's membrane and Descement's membrane. The more finely localized line C shows the energy distribution achieved with the present invention apparatus and method. Thus, the significant heating is confined to the central stroma, without undesirable heating of adjacent membranes.

Figure 5:
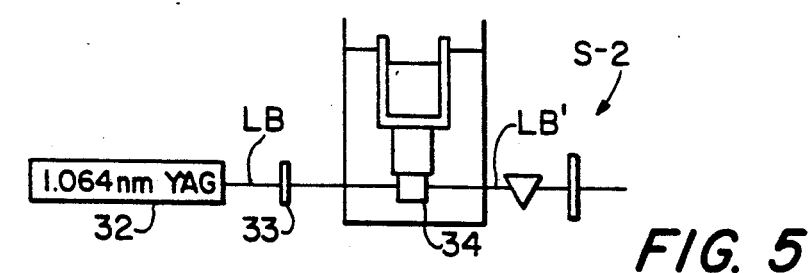
FIG. 5 is a diagrammatic view of a laser system used in one embodiment of the present invention.
Figure 6:
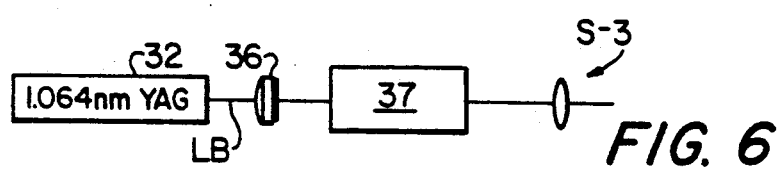
FIG. 6 is a schematic view of another embodiment of a laser system used in and forming a part of the present invention.

Referring to FIGS. 5 and 6, there are shown alternate sources S-2 and S-3 of laser beams. These emit preferably a diffraction limited beam with a wavelength in the range of 1400 to 1800 nanometers. Unlike the source S, the beam can be continuous, rather than pulsed as is the case with source S. This is possible because the radiation would be attenuated by a factor of 100 after travelling through only about one millimeter of the corneal or other tissue, due to water absorption. Since the absorption is linear and the energy deposited per unit volume varies as the reciprocal of the cubic power of the distance traversed into the corneal media, the linear energy deposition per unit volume, hence temperature, rises very sharply at the focus site. Thus, the melting process can be affected at the focus point, modifying the stromal tissue fibers in the desired localized manner, and without disturbing adjacent portions of the cornea.

One apparatus for achieving the desired wavelength generation with a continuous beam source S-2 shown in FIG. 5, in which a laser beam LB is generated by a Neodymium YAG laser 32, the laser beam LB having a wavelength of 1064 nanometers. The laser beam LB passes through a lens 33 and strikes a sodium chloride crystal 34 having f-centers, which are pumped in conventional manner, the resulting beam LB' being a tuneable near infrared beam having a wavelength range of 1400 to 1800 nanometers. Reference is made to the work of C. Pollack, 1985. In FIG. 6, the source S-3 includes the Neodymium YAG laser 32, the laser beam LB of which passes through a focussing lens 36 and into a pressurized hydrogen gas cell 37. The laser beam causes stimulated Raman scattering in the pressurized hydrogen gas cell 37 so that the incoming laser beam LB is Raman shifted from 1064 nanometer wavelength to 1900 nanometer. As will be understood, either of the continuous wave sources S-2 and S-3 may be used, instead of the pulsed wave source S shown in FIG. 1, to provide continuous wave laser beam application to the cornea, shifted toward the absorption bands in water. However, although reference has been made specifically to corneal treatment, the apparatus and method are not limited to treatment of corneas, but may be used for other general surgical purposes.

FIG. 7 discloses an alternate embodiment of a handpiece 40 for laser surgery, having, as in the handpiece 20, an outer tube 24 rotatably supported by an inner tube 26, with a terminal portion 28 having at the distal end thereof a lens 29 preceded by lens 27. An optical wedge 41 is rotatably supported in the tube 24, and caused to rotate or oscillate by any suitable apparatus. There is shown, by way of example, a miniature motor 42 which drives through gears 43a and 43b a shaft 44, on the lower end of which is a gear 45. As shown in FIG. 7a, the optical wedge 41 may be supported in an annular holder 46, having an annular gear 47 thereon which is in mesh with the drive gear 45 through an opening 49 in tube 24. The carrier 46 is rotatably supported by ball bearings 48 which engage the interior wall of the tube 24.

Referring to FIG. 8, there is shown the laser beam LB refracted by the plano-convex sapphire objective lens 29, to focus the laser beam LB at the focus spot FS which is within the cornea C. Due to the oscillatory or rotational movement of the optical wedge 41, the focus spot FS will move relative to the axis of handpiece 40 while the handpiece 40 is held stationary. Thus, the focus spot FS will move in an arc of a circle, or in a complete circular path, due to the oscillatory or rotary movement of optical wedge 41. Motion of the focus spot FS at the target site over loci in very close proximity causes a marked reduction of the plasma induction threshold; this facilitates the cutting action and increases the energy localization many-fold. This reduction of the plasma induction threshold is caused by the interception of migrating plasma-induced ions. The handpiece 40 may also be used in the dental field, where the finely focussed and moving focus spot FS enables very hard tooth enamel to be cut without either charring the enamel or heat build-up. In either surgery or dental applications, the oscillatory movement of the focus spot FS so as to reach progressively further loci along the arc is an effective method for facilitating the cutting action.

Figure 9:
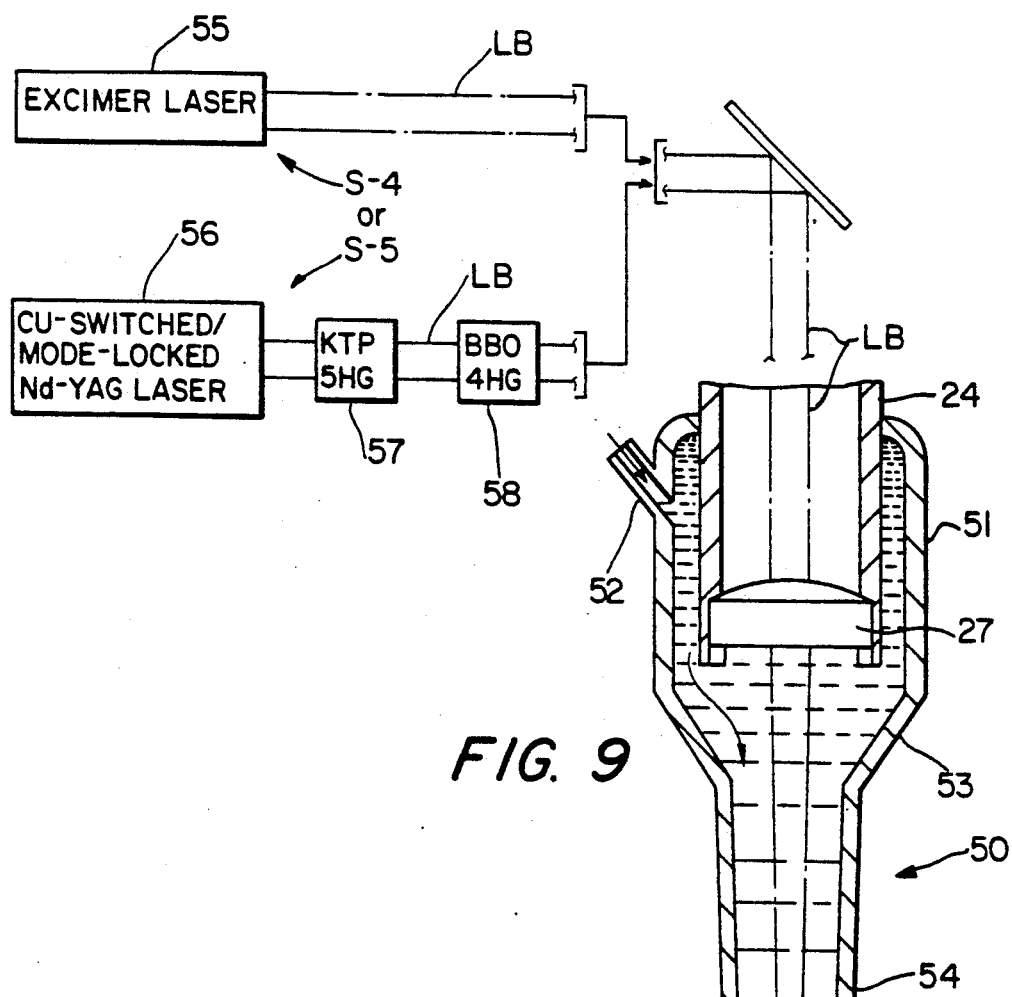
FIG. 9 is a longitudinal cross-sectional view of a modified handpiece terminal portion, and schematic representations of other sources for generating photoablative laser radiation.
Figure 10:
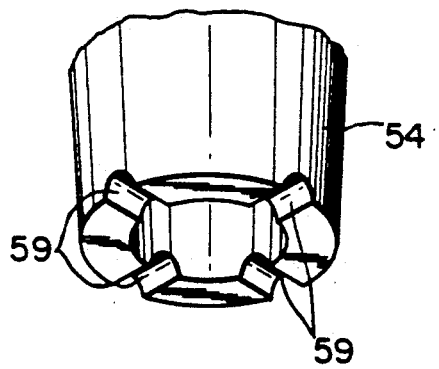
FIG. 10 is a perspective view of the distal end of the terminal portion of FIG. 9.

FIG. 9 is a view of an alternate terminal portion for a handpiece such as the handpiece 20, there being shown the outer tube 24 having a plano-convex lens 27 sealed in the distal end thereof. Objective lens 27 has a 30 mm focal length, and is of 4 mm diameter, in a preferred embodiment, providing a spot size of about ten to thirty microns. A terminal portion 50 of the handpiece has an enlarged cylinder 51 into which the end part of the outer tube 24 extends, cylinder 51 at its upper end being hermetically secured to the outer surface of outer tube 24. An inlet conduit 52 is connected to the cylinder 51 for the introduction of a fluid. Terminal portion 50 below the cylinder 51 has a tapered connecting portion 53 and below that is a conical portion 54. The distal end surface of tapered portion 54, as shown in FIG. 10, is provided with radially extending channels 59 to enable the escape of fluid from within the terminal portion 50. In use, the laser beam LB is delivered from sources described below. Normal saline solution is introduced into the terminal portion 50 through the inlet conduit 52, and substantially fills it, as shown. The radiation, after passing through the lens 27, is focussed through the column of normal saline solution. The distal end of the terminal portion 50 is engaged with the outer surface of the cornea C, and saline solution is caused to flow into terminal portion 50, across the exposure site and out through the channels 59. The escape of the saline solution aids in the removal of debris from the exposure site, preserving the optical clarity and homogeneity. The apparatus of FIGS. 9 and 10 is particularly useful where a cutting is required, such as the making of radial keratotomy cuts for the purpose of effecting correction of myopia and myopic astigmatism, although the apparatus may be used in general surgical practice. The cutting action results from the photoablative property of the excimer laser pulses from source S-4, provided by excimer laser 55: these pulses have a wavelength of 248 nanometers for a krypton fluoride laser 55, 193 nanometers for an argon fluoride laser 55, and 308 nanometers for an Xenon chloride laser 55. As will be understood, these lasers provide far UV excimer laser radiation in the TEM(oo) mode. Alternatively, a source S-5 may be utilized, comprising a Q-switched/mode-locked Neodymium YAG laser 56, which generates, as above noted, a laser beam having a wavelength of 1064 nanometers. This is delivered to a second harmonic crystal 57, which doubles the radiation to 532 nanometers: the crystal 57 is preferably potassium titanium phosphate. The radiation from the crystal 57 is delivered to a second crystal 58, where it is doubled, the crystal 58 being a fourth harmonic crystal, and may be beta barium borate. The resulting ultraviolet wavelength is at 266 nanometers. The radiation from the source S-5 will be recognized as being TEM(oo) ultraviolet radiation which has been up-converted by successive doubling caused by the second and fourth harmonic crystals 57 and 58, respectively.

Figure 11:
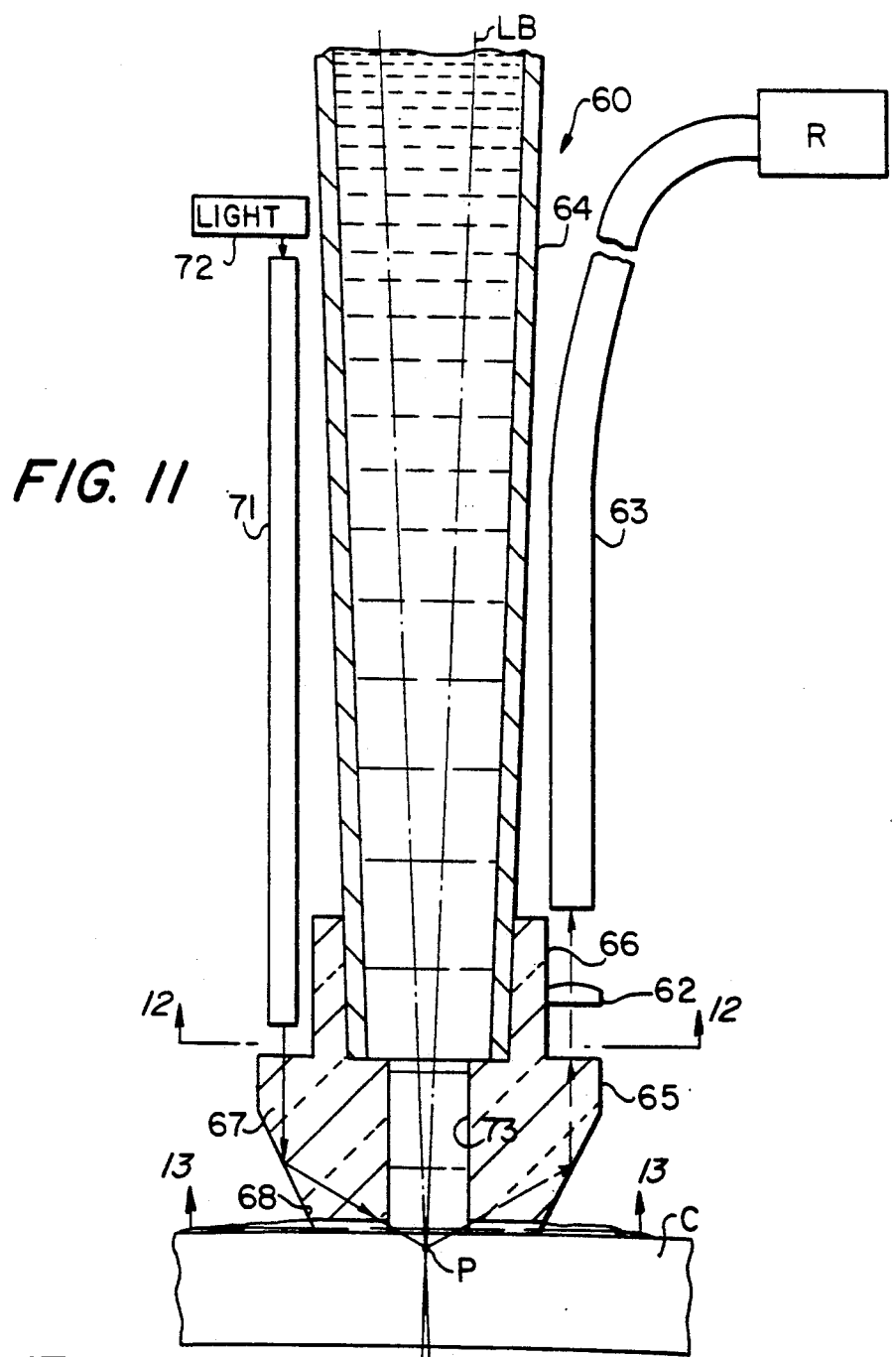
FIG. 11 is an elevational view, with parts in section, of the terminal portion of a laser handpiece and endoscope.
Figure 13:
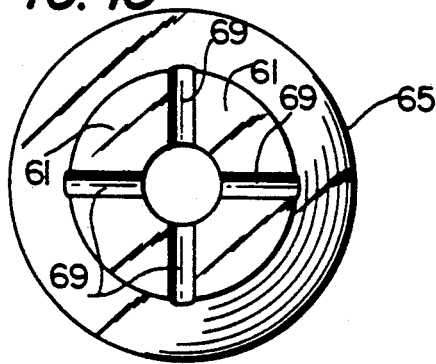
FIG. 13 is a view taken on line 13—13 of FIG. 11.
Figure 12:
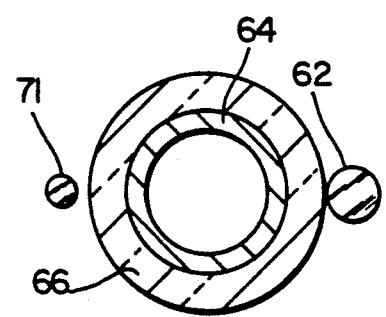
FIG. 12 is a cross-sectional view taken on line 12—12 of FIG. 11.

There is shown in FIG. 11 a terminal portion 60 which includes a tapered portion 64, shown filled with a liquid such as a normal saline solution, and having a laser beam LB passing axially thereof, focussing beyond the distal end and in a cornea C. The lower end of the tapered portion 64 is inserted into a socket formed by sleeve 66 (see also FIG. 12) of a glass contact tip 65. The sleeve 66 extends upwardly from a solid internally reflective conical glass element 67 having internal reflection at surface 68. The distal end of the conical element 67 is provided, as shown in FIG. 13, with channels 69 for the escape of the saline solution. Between the channels 69 are contact surfaces 61 which are transverse of the axis of the contact tip 65 and are polished optically clear, as is the cylindrical surface of conical element 67. A single multimode fiber 71 adjacent tube 64 receives illumination from a light source 72, the light being transmitted into the glass contact tip 65 and illuminating the penetration point P of the ablative laser radiation provided by laser beam LB. The image of the penetration point P is transmitted to the reflecting surface 68, and thence through the coupling lens 62 to a fine coherent fiberoptic bundle 63. The fiberoptic bundle 63 conveys the image to any receiver R desired, such as to monitoring and display elements and penetration control components (not shown). Since the inner core or passage 73 of the contact tip 65 is filled with fluid, such as the normal saline solution, index matching occurs at the interfaces and an image of the penetration point P is readily obtained by the contact tip 65, coupling lens 62 and fiberoptic bundle 63.

In FIGS. 14–16, there is shown an embodiment of a terminal portion 80 of a probe useful for conducting ophthalmic intraocular, in particular, cataract surgery. As will be understood, the terminal portion 80 replaces the terminal portion of the handpiece 20 beyond the lens 27. There are provided slightly diverging lens 81 which receives the laser beam LB, the spreading beam then passing into a quartz rod 82 which is cylindrical, and has a beveled distal end surface 83. The quarts rod 82 conveys the laser radiation by means of total internal reflection to the beveled end surface 83, where the radiation leaves the instrument and is sharply defined into a circular or semi-circular radiation distribution area A (shown rotated for clarity). The quartz rod 82 is housed within a generally elliptical tube 84 which is preferably a tight sealing rubber silicon sheath having an inlet conduit 85 connection to an internal passage 86 lying between the wall of the tube 84 and the quartz rod 82, the outlet end of passage 86 having a shape defined by two curved walls, as shown in FIG. 15. Preferably, a discharge tube 87 is inserted part way into the tube 84 from the distal end thereof, to define the discharge port of the passage 86. Opposite the passage 86, there is an aspiration passage 88 having an aspiration conduit 89 connected to its end opposite the distal end, there being provided at the distal end of aspiration passage 88 a tubular extension 91. As shown in FIG. 15, the ends of the discharge tube 87 and the tubular extension 91 are beveled, and lie in the same plane as the beveled end surface 83 of quartz rod 82. The relative locations of the passage 86, beveled end surface 83 and the entry port of aspiration passage 88 are shown in FIG. 16.

The beveled end surface 83 causes the radiation distribution area A to lie displaced from the geometric axis of quartz rod 82 and at or towards the geometric axis of the passage 88. Tissue fragments TF which are drawn towards the aspiration passage 88 are subjected to the energy in radiation distribution area A, and are cut by the ablative radiation. Saline solution which enters the passage 86 is discharged adjacent to and flows across the beveled end surface 83 toward the entry port of aspiration passage 88, to remove debris.

FIG. 17 discloses an alternate embodiment of probe, in which the silicon tube or sheath 94 has the quartz rod 82 in it, with, as shown in FIG. 18, the longitudinal axis of the cylindrical quartz rod 82 and the major longitudinal axis of elliptical sheath 94 coinciding. There are thereby provided an infusion passage 96, and an aspiration passage 98 in the equal-area spaces between the quartz rod 82 and sheath 94. The sheath 94 has the distal end thereof beveled, as shown in FIG. 17, and the end face 83 of quartz rod 82 lies in the plane of the beveled end of sheath 94. The longer end portion 97 of sheath 94 which forms the entrance to the aspiration passage 98 may have other shapes than as shown in FIG. 17, i.e. it may be angled as shown in FIG. 19.

Figure 19:
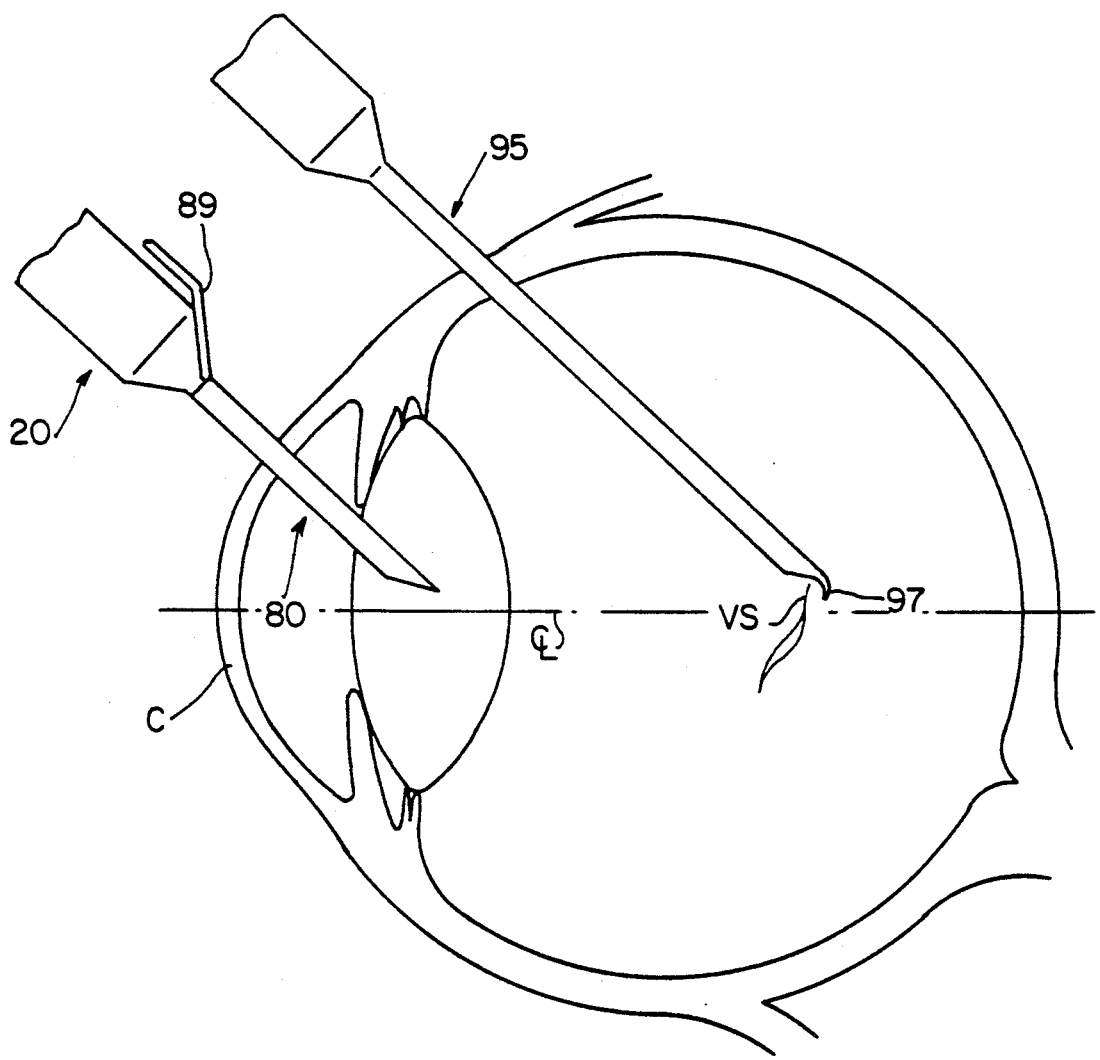
FIG. 19 shows probes in accordance with FIGS. 14 and 17 in use.

FIG. 19 shows the application of the tips of FIGS. 14 and 17 to cataract surgery and to vitreal strand removal or vitrectomy, respectively. For cataract surgery, there is inserted through the cornea C and into the cataractous lens CL the terminal portion 80 of a handpiece. Photoablative laser energy, as above described, is delivered to the cataractous lens CL, to cause its disintegration, and the ablated lens is withdrawn through the aspiration conduit 89. Because of the localized character of the photoablative laser energy delivered to the lens, there are avoided such undesirable effects as the possibility of burning of the cornea and the possible shattering effect of the nucleus of the corneal endothelium resulting in corneal endothelial decomposition, hazards present in the currently used techniques of cataract extraction.

For vitrectomy, the terminal portion 95 of the probe shown in FIGS. 17 and 18 is inserted through the pars plana and is used to cut vitreal strands VS. Preferably, the end 97 of the sheath 94 is bent at an angle, as shown in FIG. 19, so as to enhance the lateral flow of vitreous strands across the radiation distribution area A of the cutting ablative radiation source which is emitted from the end surface of the quartz rod 82.

It will be obvious to those skilled in the art that various changes may be made in the herein disclosed method and apparatus. However, the invention is not limited to what is set forth in the specification or described in the drawings, but only as defined in the claims appended hereto.

What is claimed is:

1. Apparatus for delivering laser energy comprising:
   means for generating a laser beam in TEM(oo) mode,
   a hand piece for receiving said laser beam having proximal and distal ends, and an axis and,
   means in said handpiece for focusing said beam to a focus spot beyond said handpiece and positioned a predetermined distance from said focussing means, whereby to effect modification of a site within a body through a portion of which said beam has passed.

2. The apparatus of claim 1, wherein said focussing means comprises means for focussing said focus spot approximately 0.4–0.5 millimeter from said focussing means.

3. The apparatus of claim 1, said laser beam generating means comprising means for generating a laser beam having a wavelength of approximately 1.0 to 2.0 microns.

4. The apparatus of claim 1, said generating means comprising means for generating a continuous laser beam.

5. The apparatus of claim 1, wherein said generating means comprises means for generating a continuous laser beam having a wavelength of approximately 1,400 to 1,800 nanometer.

6. The apparatus of claim 1, said means for generating a laser beam comprising excimer laser means for generating a photoablative laser beam having a wavelength of approximately 193–300 nanometers.

7. The apparatus of claim 1, said generating means comprising means for generating a laser beam having a wavelength of approximately 1064 nanometer.

8. The apparatus of claim 7, said generating means generating a pulsed laser beam.

9. The apparatus of claim 6, said generating means comprising means for providing pulses having a duration of not substantially in excess of about 70 nanoseconds.

10. The apparatus of claim 9, said generating means comprising means for delivering said pulses at a rate of approximately 2,000 per second.

11. The apparatus of claim 1, said means for generating a laser beam comprising YAG laser means for generating pulsed radiation at a wavelength and frequency, and means for reducing the wavelength of the generated radiation.

12. The apparatus of claim 11, said wavelength reducing means comprising means for doubling said frequency.

13. The apparatus of claim 11, said wavelength reducing means comprising a crystal through which said radiation is passed.

14. The apparatus of claim 11, said wavelength reducing means comprising a second harmonic crystal and a fourth harmonic crystal positioned to successively receive radiation from said YAG laser means.

15. The apparatus of claim 14, said second harmonic crystal being potassium titanium phosphate.

16. The apparatus of claim 15, said fourth harmonic crystal being beta barium borate.

17. The apparatus of claim 14, said fourth harmonic crystal being beta barium borate.

18. The apparatus of claim 1, said focussing means comprising a plano-convex lens.

19. The apparatus of claim 18, wherein said plano-convex lens is a sapphire lens in the distal end of said handpiece and the plano surface thereof being an exterior lens surface which is engageable with a body containing said focus spot.

20. The apparatus of claim 1, and further comprising means for moving said focus spot relative to the axis of said handpiece.

21. The apparatus of claim 20, said moving means comprising an optical wedge, and means for imparting rotational motion to said optical wedge.

22. Apparatus for delivering laser energy as set forth in claim 1, wherein said means in said handpiece for focussing said beam comprises means for focussing said beam to a focus spot having a diameter of substantially a few microns.

23. Apparatus for performing laser surgery comprising:
   a handpiece having proximal and distal ends,
   means for introducing a laser beam into said proximal end,
   means in said handpiece for focussing said beam to a focus spot including an objective lens at said distal end,
   said handpiece having a tubular terminal portion, with an open distal end, said terminal portion extending beyond the distal end of said handpiece and coaxially with said objective lens for engaging a body, said objective lens being spaced from the distal end of said terminal portion, and
   means for causing a flow of liquid through the tubular terminal portion and out of the distal end thereof,
   whereby said objective lens is spaced a predetermined distance from said body and said laser beam passes through the liquid in said tubular terminal portion.

24. The apparatus of claim 23, wherein said distal end of said tubular terminal portion has a distal end surface for engagement with a body, said distal end surface having lateral escape channels therein.

25. The apparatus of claim 24, wherein said tubular terminal portion narrows towards said distal end thereof.

26. The apparatus of claim 23, said generating means comprising means for generating ablative laser radiation, said apparatus further comprising means for delivering light to a body adjacent said handpiece, and means for acquiring an image of said body.

27. The apparatus of claim 26, said light delivering and image acquiring means comprising a transparent element at the distal end of said tubular terminal portion having distal end surface means adapted for engaging a surface of said body.

28. The apparatus of claim 27, said handpiece having a longitudinal axis, said element having an internal reflective surface inclined relative to said longitudinal axis for reflecting light delivered to said element and for reflecting an image of said body.

29. The apparatus of claim 31, said light delivering means comprising optical fiber means for delivering light to said element, said optical fiber means having an axis and an end adjacent said element with the axis thereof laterally of said longitudinal axis.

30. The apparatus of claim 28, said image acquiring means comprising optical fiber means for receiving and transmitting an image of said body, said optical fiber means having an axis and an end adjacent said element with the axis thereof laterally of said longitudinal axis.

31. The apparatus of claim 27, said element being of substantially inelastic material and having a fluid passage therethrough extending transversely of said distal end surface, said tubular terminal portion having said element thereon at the distal end thereof, means for introducing liquid into said tubular terminal portion remote from said element, said fluid passage in said element being in fluid communication with the interior of said tubular terminal portion.

32. The apparatus of claim 31, wherein said passage of said element is a linearly extending passage substantially coaxial with the axis of said tubular terminal portion.

33. The apparatus of claim 31, said element having a distal surface and lateral channels in the distal surface thereof in communication with said passage.

34. Apparatus for delivery of laser energy comprising:
a probe comprising a substantially cylindrical quartz rod having proximal and distal ends,
said quartz rod at the distal end thereof having a beveled end surface for emitting radiation, and
means for delivering a divergent beam of laser radiation to said proximal end of said quartz rod and for causing radiation to be conveyed through said rod by internal reflection, and
means for causing fluid to flow across said bevelled end surface of said rod comprising:
(a) means for discharging fluid from said probe at the distal end thereof comprising a discharge port which is beveled and lies in the same plane as the bevelled end surface of said quartz rod,
(b) means for aspirating fluid from the vicinity of the distal end of said probe comprising an aspiration port which has a bevelled end portion which lies in the same plane as the bevelled end surface of said quartz rod, said bevelled end surface of said rod being between said ports,
whereby the radiation emitted from said quartz rod is sharply defined beyond said bevelled end surface.

35. The apparatus of claim 34, said tube having said quartz rod centrally located therein.

36. The apparatus of claim 34, said probe comprising a tube, said quartz rod being in said tube, said fluid discharging means and said fluid aspirating means comprising passages in said tube adjacent said quartz rod, said quartz rod being between said passages.

37. The apparatus of claim 36, said tube being of silicon rubber.

38. The apparatus of claim 34, said tube being elliptical.

39. The apparatus of claim 38, said tube having said quartz rod centrally located therein.

40. A method of surgically cutting or modifying only tissue which is located at a short, predetermined distance from the surface thereof comprising:
providing a handpiece having a distal end with a focussing lens at a distal end thereof,
placing against the surface of said tissue the focussing lens at the distal end of said handpiece,
generating a laser beam in TEM(oo) mode,
passing said laser beam through said handpiece toward and through said focussing lens at said distal end and thence into said tissue with said lens thereagainst, and
cutting or modifying only said tissue at a distance from said surface by focussing said laser beam to a focus spot located a short distance into said tissue from the surface thereof.

41. The method of claim 40, wherein said generating is of a pulsed laser beam having a wavelength of 0.2 to 2.0 microns, the pulses having a duration of not substantially in excess of about 70 nanoseconds.

42. The method of claim 40, wherein said generating is of a continuous laser beam.

43. The method of claim 40, wherein said generating is of a laser beam having a wavelength of about 0.2–2.0 microns.

44. The method of claim 40, wherein said generating is of pulses of laser radiation.

45. The method of claim 44, wherein said generated pulses having a duration of not substantially in excess of about 70 nanoseconds.

46. The method of claim 44, wherein said generating is of a laser beam having a wavelength of approximately 1064 nanometers.

47. The method of claim 44, wherein said generating is of a laser beam having a wavelength of 1400 to 1800 nanometers.

48. The method of claim 40, and further comprising moving said focus spot in said tissue.

49. The method of claim 48, wherein said moving is movement in an arcuate path.

50. The method of surgically cutting or modifying only tissue as set forth in claim 40 wherein said cutting or modifying only said tissue is by focussing said laser beam to a focus spot having a diameter of substantially a few microns.

51. A method of surgically cutting or modifying tissue comprising:
generating a laser beam of photoablative property in TEM(oo) mode;
directing said beam into a handpiece and thence into and partially through tissue and focussing said beam to a focus spot at an exposure site in said tissue a predetermined distance from the surface thereof.

52. A method of surgically cutting or modifying tissue as set forth in claim 51, wherein said focussing of said beam comprises focussing said beam to a focus spot having a diameter of substantially a few microns.

53. A method of surgically cutting or modifying a body having a surface with an exposure site comprising:
generating a laser beam of photoablative property in TEM(oo) mode;
directing said laser beam into a handpiece having therein focussing means including an objective lens for forming a focus spot,
placing said objective lens a predetermined distance from said surface with said exposure site such that said focus spot is at a predetermined position relative to said exposure site, and
causing a stream of liquid to move across said exposure site.

54. The method of claim 53, including providing a body of liquid between said objective lens and said exposure site, and passing said beam through said body of liquid.

55. The method of claim 54 and further comprising causing said body of liquid to flow towards said exposure site.

56. The method of claim 51, and further comprising directing light to said exposure site, and acquiring an image of said site at a location remote therefrom.

57. A method of surgically cutting or modifying a body as set forth in claim 53, wherein said directing of said laser beam is into a handpiece having therein focussing means including an objective lens for forming a focus spot of substantially a few microns.

58. A method of treatment of the human body comprising:
generating a beam of TEM(oo) mode laser radiation,
conducting said beam through a laser radiation transmitting rod having a distal end,
causing said beam to be internally reflected in said rod and to pass out of the distal end thereof,
focussing said beam at a location beyond the distal end of said rod, and
causing fluid to flow across said distal end of said rod.

59. The method of claim 40, wherein said placing against the surface of tissue is placing against the epithelium of a cornea, and said focussing of said laser beam is in the intrastromal layer, whereby to cause localized heating of stromal fibers.

60. The method of claim 51, wherein said focussing of said laser beam is into the intrastromal layer of a cornea, whereby to cause localized heating of stromal fibers.

61. A method of modifying the stroma comprising:
generating a laser beam of photoablative property in the TEM(oo) mode;
directing said laser beam into a handpiece and thence into a cornea, and through a portion of the thickness thereof, and
focussing said laser beam to a focus spot located in the intrastromal layer,
whereby only the intrastromal layer is modified by said laser beam.

62. The method of modifying the stroma as set forth in claim 61, wherein said focussing of said laser beam is to a focus spot having a diameter of substantially a few microns.

* * * * *